United States Patent [19]
Bedner et al.

[11] Patent Number: 6,139,526
[45] Date of Patent: Oct. 31, 2000

[54] SINGLE USE SELF DISABLING SAFETY SYRINGE

[76] Inventors: Richard J. Bedner, 113 Smoke Rise Dr., Warren, N.J. 07060; Radu Saftoiu, Bailey Hollow Rd., Morristown, N.J. 07900

[21] Appl. No.: 09/356,019

[22] Filed: Jul. 16, 1999

Related U.S. Application Data

[63] Continuation of application No. 09/164,992, Oct. 1, 1998, abandoned.

[51] Int. Cl.⁷ ...................................................... A61M 5/00
[52] U.S. Cl. ........................................... 604/110; 604/218
[58] Field of Search .................................... 604/218, 228, 604/110, 187

[56] References Cited

U.S. PATENT DOCUMENTS 5,643,211   7/1997   Sadowski et al. .................. 604/218 X

*Primary Examiner*—John D. Yasko
*Attorney, Agent, or Firm*—Robert A. Green

[57] ABSTRACT

The disclosure is of a syringe including a barrel containing an injectibe fluid and a plunger for moving the fluid. The barrel is made up of two parts which are held together in the barrel during an injection and after the injection has been made, the plunger is separated into its component parts and cannot be reassembled and used again.

1 Claim, 6 Drawing Sheets

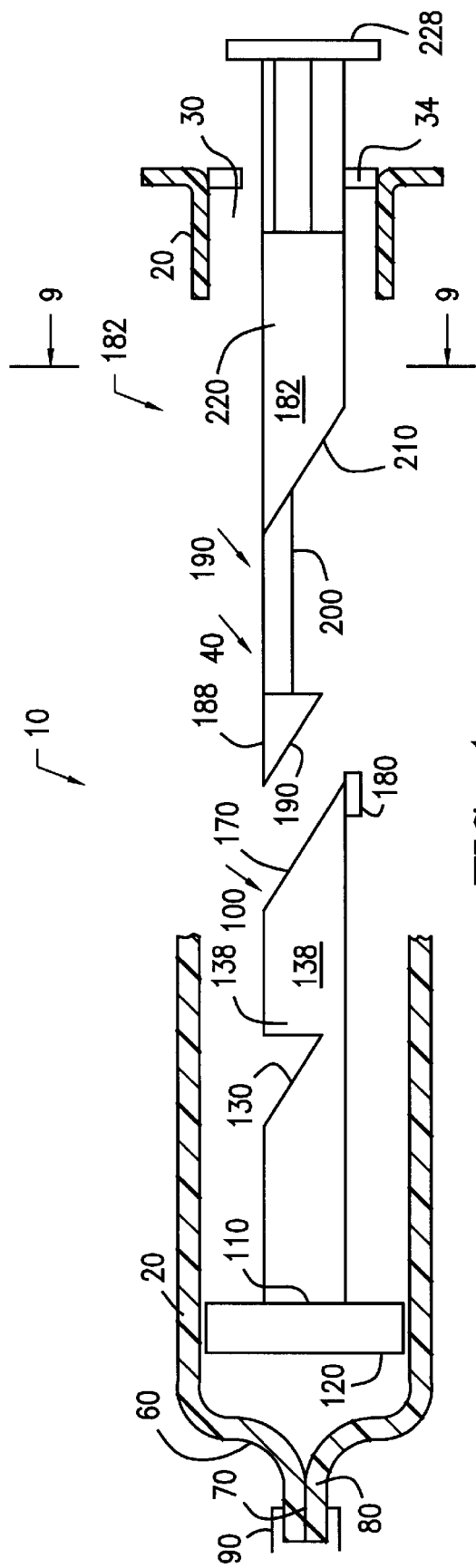
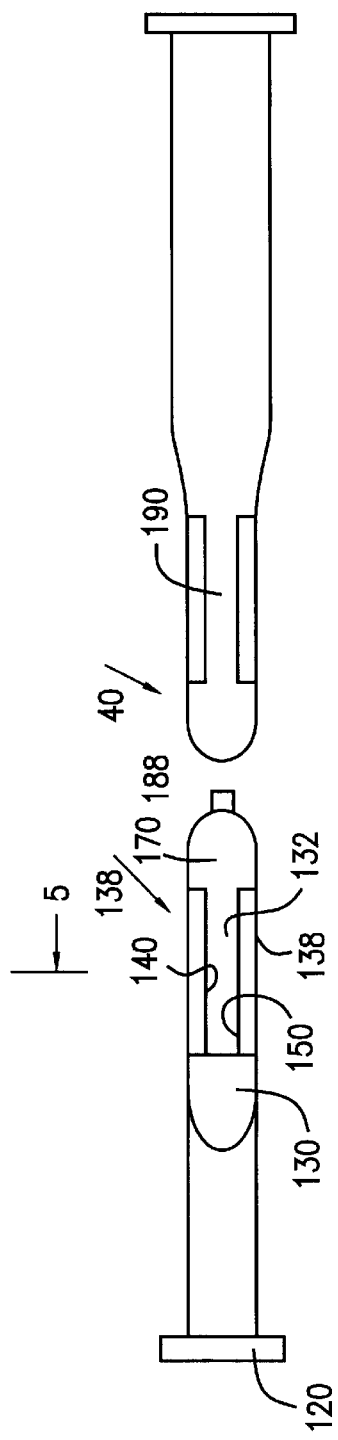
FIG. 1
FIG. 2

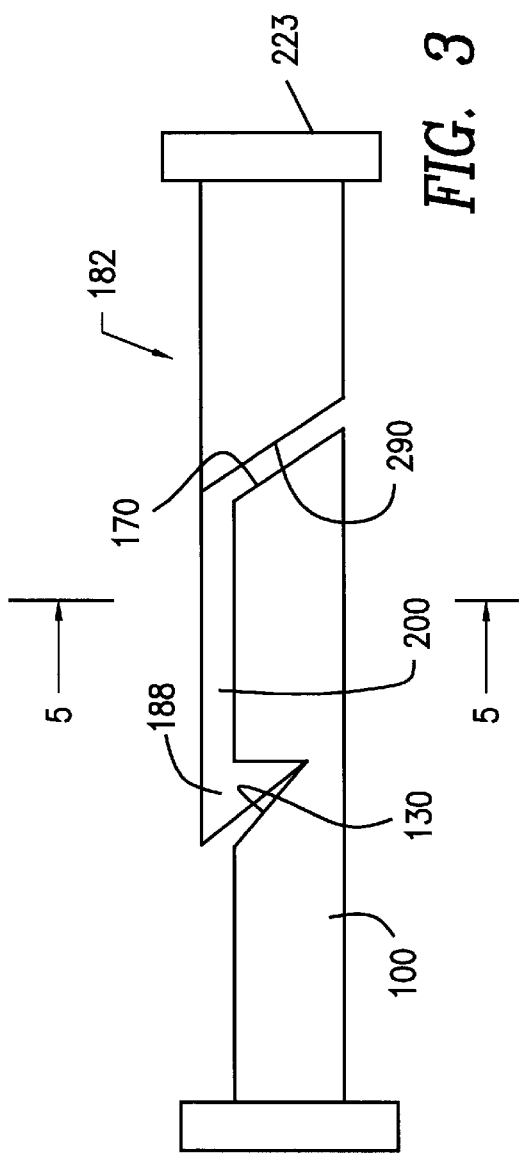
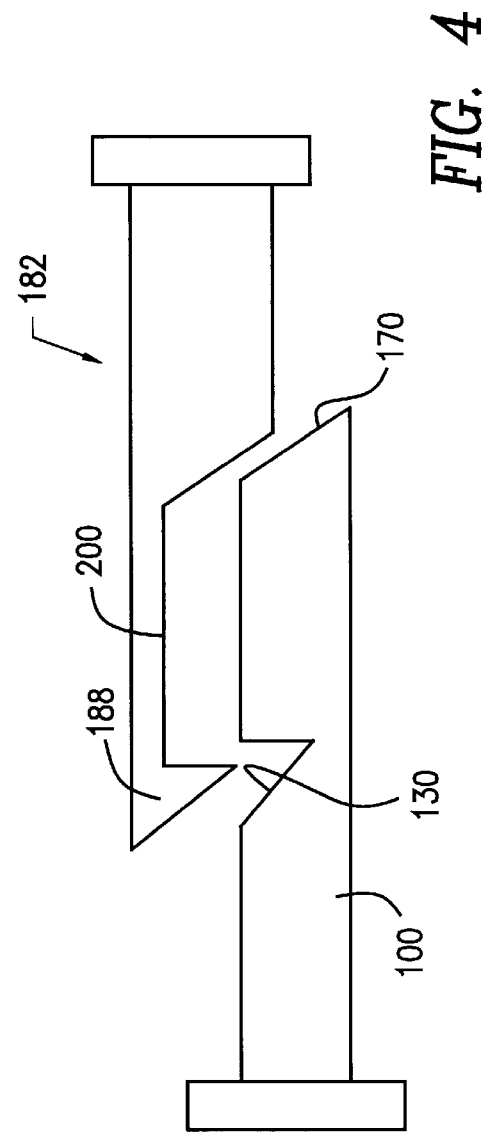

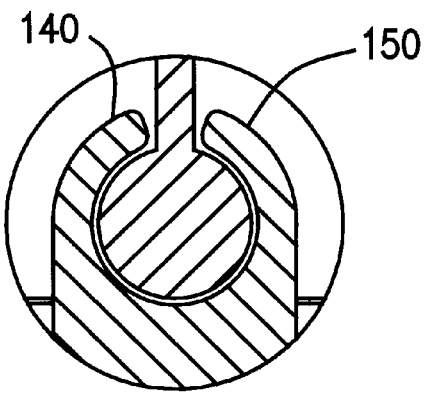
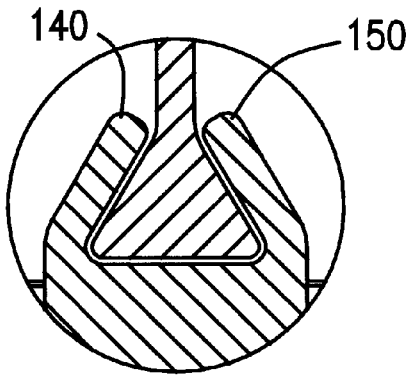
FIG. 5    FIG. 6
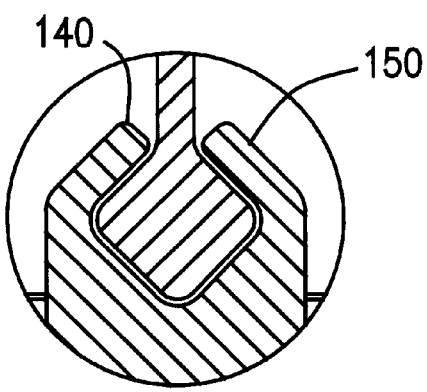
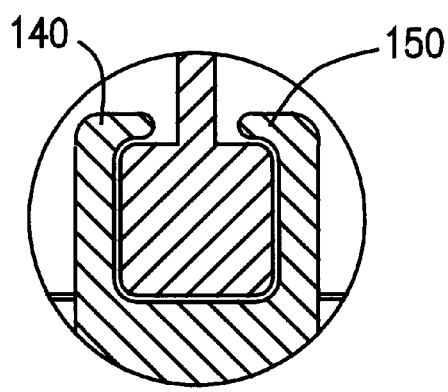
FIG. 7    FIG. 8

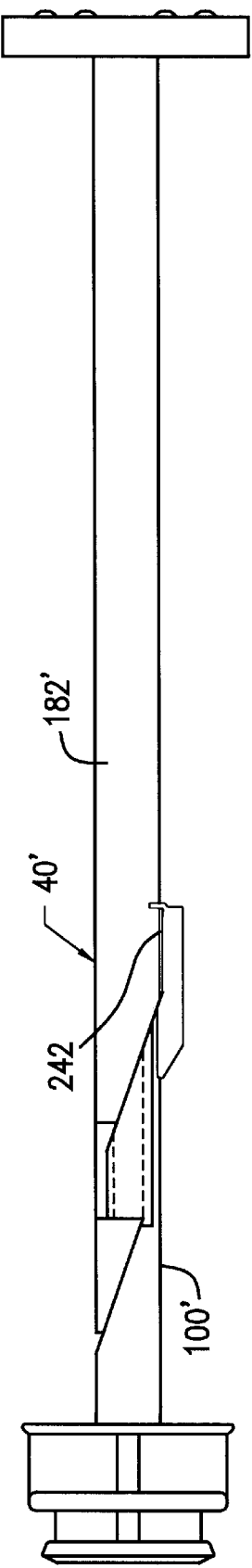
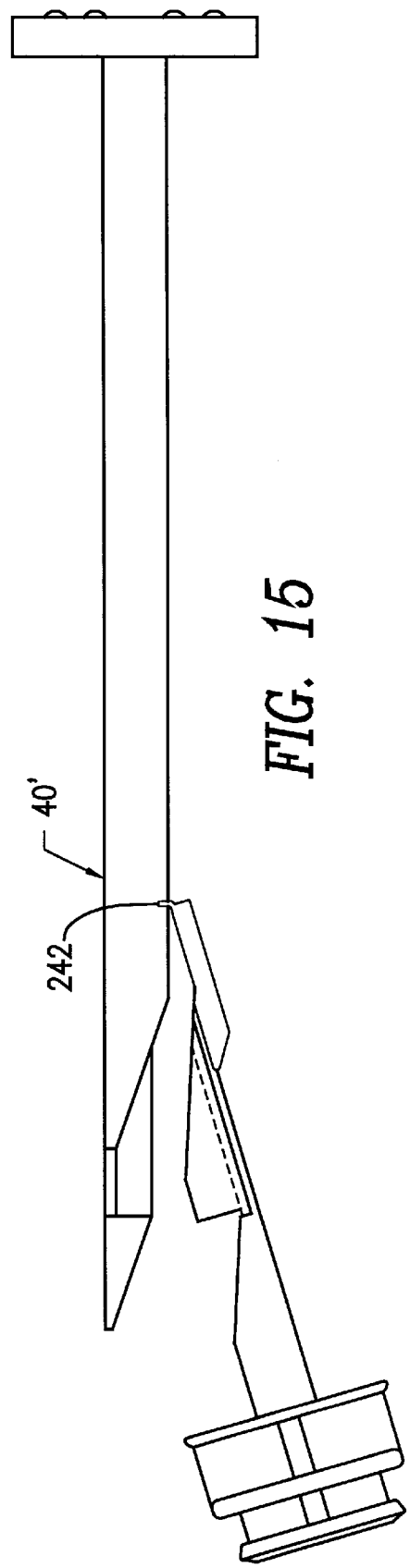

SINGLE USE SELF DISABLING SAFETY SYRINGE

This is a continuation of application Ser. No. 09/164,992 filed Oct. 01, 1998 now abandoned.

BACKGROUND OF THE INVENTION

For years, the medical profession has needed a hypodermic syringe which could be used only once and could not be cycled again for a second use and would thus, in effect, be disposable. However, no completely satisfactory syringe of this type has been devised. The present invention provides a single use syringe of relatively simple construction.

SUMMARY OF THE INVENTION

A single use syringe embodying the invention includes a collapsibl plunger which is mounted inside a cylinder or barrel which contains a fluid and from which the fluid can be dispensed. The plunger is used in normal fashion by being pushed into the barrel to dispense the fluid from the barrel and then it is further pushed into the plunger until the plunger is collapsed into separate pieces which cannot be re-assembled for re-use.

DESCRIPTION OF THE DRAWINGS

FIG. 1 is a side elevational view of a hypodermic syringe embodying the invention with its plunger shown diassembled;

FIG. 2 is a plan view of the hypodermic syringe of FIG. 1 showing portions thereof;

FIG. 3 is a side elevational view of the plunger in FIG. 1 shown assembled;

FIG. 4 is a side elevational view of the plunger of FIG. 3 illustrating one stage in its operation;

FIG. 5 is a sectional view along the lines 5—5 in FIG. 2;

FIG. 6 is a view similar to that of FIG. 5 showing a modification in the form of a portion of the plunger of the invention;

FIG. 7 is a view similar to that of FIG. 5 showing another modification of the invention;

FIG. 8 is a view similar to that of FIG. 5 showing another modification of the invention.

FIG. 14 is a side elevational view of a modification of the invention, and

FIG. 15 is a sectional view of a portion of the invention illustrating operation thereof.

DESCRIPTION OF THE INVENTION

Figure 9:
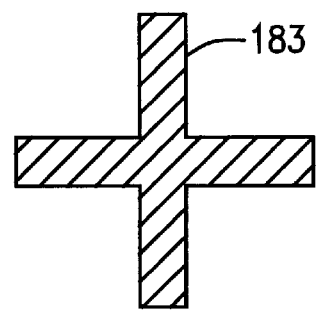
FIGS. 9, 10, and 11 are sectional views along the lines 9—9 in FIG. 1 illustrating some modification in this portion of the plunger of the invention.

Referring to FIGS. 1 and 2, a hypodermic syringe 10 embodying the invention is made of glass, plastic or any other suitable material although plastic is preferred at the present time. The syringe includes a convention barrel 20 which has an open end 30 into which a piston or plunger 40 embodying the invention is inserted with an interference fit therewith. The opposite end of the barrel has an end wall 60 which has a fluid-dispensing opening 70 which communicates with a generally tubular member 80 secured to the outside of the wall 60 and to which a hypodermic needle 90 is permanently or removably attached. This portion of the invention is of conventional, well-known form.

Referring to FIGS. 1 and 2, the plunger 40 embodying the invention includes a first or leading portion 100 which, in one form of the invention, has a generally circular cross section. However, any suitable cross section which will operate satisfactorily may be used. The leading portion 100' has a leading end 110 which is secured to a disk 120 having substantially the same diameter as the inner diameter of the barrel 20 so that it is slidable in the barrel and can force fluid out of the barrel.

Somewhat rearwardly of the disk 120, the top surface of the leading portion 100 of the plunger is cut out to form a first ramp 130 which extends downwardly and slopes (negatively) toward the rear and joins and communicates with a tubular portion 138. The tubular portion 138 extends rearwardly a short distance and at its rear end it tapers downwardly at a negative slope to provide a second ramp 170.

Rearwardly of the ramp 130, the wall of the tubular portion 138 is provided with a slot 132 which is defined by relatively closely spaced wall portions 140 and 150 (FIG. 5). The plunger is of a suitable material so that the wall portions 140 and 150 can be spread apart slightly so that a second portion of the plunger can be inserted into the tubular portion 138 as described below.

The rearward portion 182 of the plunger includes a leading portion 188 which has a sloped front end 190 whose slope matches the slopes 130 and 170. The portion 188 is coupled to the rear portion 220 and and to a leading sloped front wall 210 thereof. The coupling of front portion 188 and rear portion 220 is a thin rib 191 which is a portion of the wall of portion 182 of the portion 220. A tubular or cylindrical member 200 hangs down from the rib 191. Rib 191 and tube 200 are connected together along their lengths and they lead to a negatively sloped wall 210 which is the leading end of the rear portion 220 of the second portion 182 of the plunger.

Various forms of this portion of the invention are shown in FIGS. 5 to 8.

The end of the second portion 182 which lies outside the barrel 20 carries a relatively large-area disk 220 by which an operator manipulates the plunger inside the barrel. When the two parts of the syringe are assembled, as seen in FIG. 3, the second portion 182 rests on the first portion 100 with portion 188 seated on ramp 130 and wall 210 bears against wall 170 and the rib cylinder 200 is seated between the walls 140 and 150.

In using the hypodermic syringe of the invention 10 the assembled plunger 40, as illustrated in FIG. 3, is mounted inside the barrel 20 and the plunger is manipulated, in conventional fashion, to draw fluid from a source through the needle 90 into the cylinder. Next, the plunger is pushed into the barrel and the fluid is pushed forwardly toward the wall 60 and the desired fluid is fed from the barrel and needle 90 into a patient.

Referring to FIG. 4, after the injection has been made and at the conclusion of the injection, the plunger is pushed forwardly still further and as it bears against the end wall 60 its forward motion is stopped. However, the upper portion of the plunger continues to move forwardly and the two ramps 190 and 210 move up the ramps 130 and 170 until the upper portion of the plunger is forced out of the portion 182 and it is separated from the lower portion of the plunger. Thus separated, the two portions cannot be rejoined.

Figure 10:
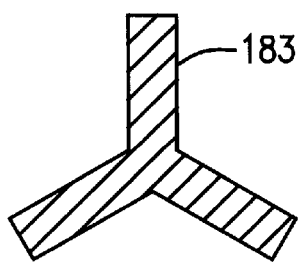
Figure 11:
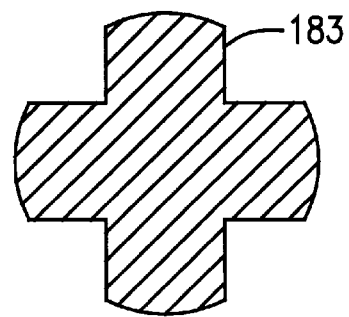

The rib 191 and cylinder 200 structure may have any suitable cross section as illustrated in FIGS. 5 to 8. In addition, the cylinder 183 may have any suitable cross section as illustrated in FIG. 9 to 11 along line 9—9.

Figure 13:
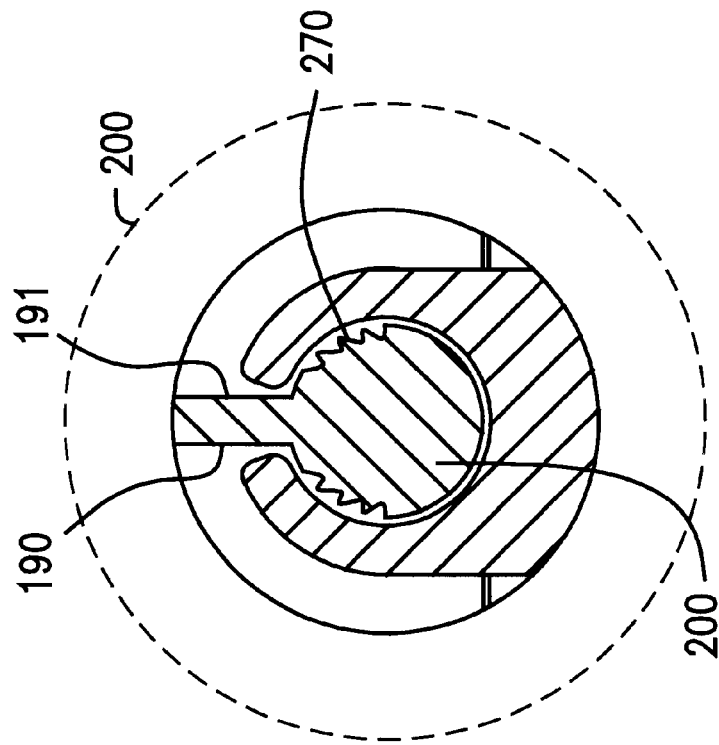
FIGS. 12 and 13 are sectional views simimlar to that of FIG. 5 illustrating modifications in this portion of the invention.
Figure 12:
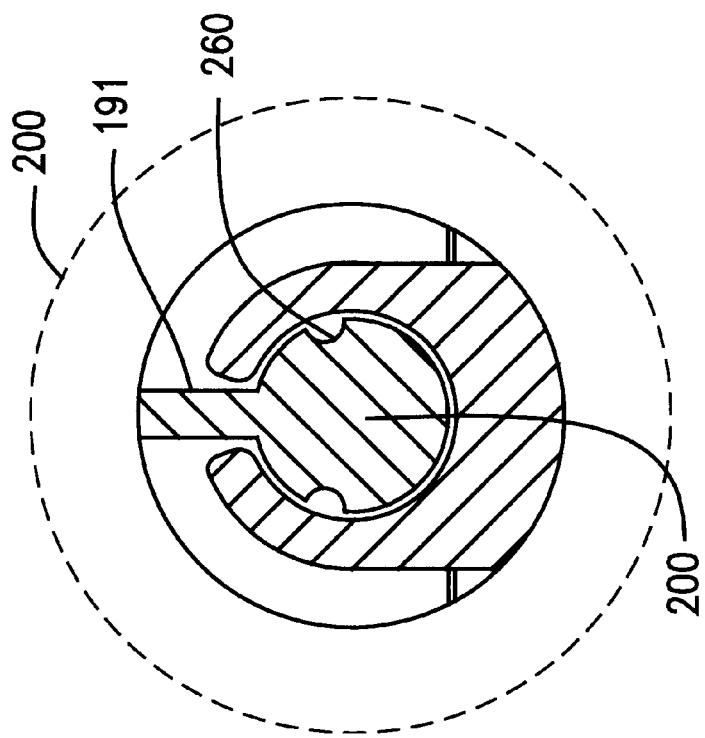

In another form of the invention, the cylinder 200 associated with the tab 191 may have its surface serrated as shown at 260 in FIG. 12 or it may have one or more longitudinal slots 270 in its surface as shown in FIG. 13. The serrations and the slots can be sensed or felt by an operator as he pushes the plunger forwardly and he can thus discontinue using and disabling the plunger if he wishes.

In a modification of the plunger of the invention, referring to FIG. 14, a plunger 40' includes upper portion 182' and lower portion 100' which may be molded if feasible or desirable and they are releasably coupled together by a living hinge. In one form, refering to FIG. 14, the living hinge comprises a small pin 242 formed on portion 182' and a hole formed in portion 182' into which the pin 242 may be snapped. The two parts 100' and 1282' being thus coupled together can be easily separated by having the pin 242 broken. When the two parts are coupled together they are inserted in the barrel of the hypodermic and disconnected when the barrel is operated as described above.

It is clear that the pin 242 and hole 240 are located properly so that the proper operation of the piston can be achieved.

The invention also includes a form which provides "tactile feel" in operation of the syringe. This means that the operator can feel the progress of the operation of the plunger and can discontinue insertion thereof if desired before the plunger is broken apart.

In this aspect of the invention, referring to FIGS. 12 and 13, the cylinder 200 attached to rib 191, has its surface formed with one or more slots as in FIG. 12 or with serrations as in FIG. 13. In using the syringe with one of these formations in the cylinder 200, as the plunger is operated, portion 182 rides up ramps and the cylinder 200 engages the wall portions and spreads them apart and the feel the slots or serrations and the operator similarly feels them and can discontinue the operation if desired.

In a modification of the plunger of the invention, referring to FIG. 14, a plunger 40' includes upper portion 192' and lower portion 100' which may be molded together if feasible or desirable and they are releasably coupled together by a living hinge 250. In one form, referring to FIG. 14, the living hinge comprises a small pin 242 formed on portion 182" and a hole 240 formed in portion 182' inteo which the pin 242 may be snapped. The two parts 100' and 128' being thus coupled together can be easily separated by having pin 242 broken. When the two parts are coupled together, they are inserted into the barrel of the hypodermic and broken apart when the syringe is operated as described above.

It is clear that the pin 242 and hole 240 are positioned so that the proper operation of the piston can be achieved.

What is claimed is:

1. A single use hypodermic syringe comprising
 a generally tubular envelope adapted to contain a fluid to be dispensed and containing a plunger for dispensing said fluid,
 said tubular envelope having a front dispensing end and a dispensing needle coupled to said front end, said front end having means for stopping the motion of said plunger after fluid has been dispensed,
 said plunger including an upper elongated member and a lower elongated member positioned with said upper member overlying said lower member and adapted to slide with respect to each other,
 said upper and lower members having engaging parts adapted to permit said upper and lower members to engage each other and to move as a unit toward said fluid dispensing end of said envelope as a fluid dispensing operation is performed, said engaging parts including a hook-like process on said upper member and a depression in the top surface of said lower member in which said hook-like process is seated when said plunger is in position to perform a dispensing operation,
 said upper member having a slanted wall positioned at its rear end and said lower member having a slanted wall at its front end, said slanted walls engaging each other and assisting in causing said plunger to move forwardly in said envelope in performing a dispensing operation,
 said lower member having a front end adapted to engage and bear against said front end of said envelope as a stop to stop the forward motion thereof,
 said upper member having an enlarged end wall outside said envelope usable for manually pressing said plunger forwardly as a unit inside said envelope in performing a fluid dispensing operation,
 said upper member being seated on said lower member as described preparatory to performing a fluid dispensing operation, at the end of which continued dispensing pressure applied to said enlarged end wall forces said hook-like process to slide on said lower member out of said notch whereby said upper member slides away from and out of contact with said lower member and is thus permanently out of contact therewith and no additional dispensing operation can be performed thereby.

* * * * *